US012484932B2

(12) United States Patent
Doerr et al.

(10) Patent No.: US 12,484,932 B2
(45) Date of Patent: Dec. 2, 2025

(54) LAPAROSCOPIC HYSTERECTOMY SPECIMEN RETRIEVAL DEVICE

(71) Applicants: Daniel Doerr, Orlando, FL (US); Gary Haberland, Winter Park, FL (US)

(72) Inventors: Daniel Doerr, Orlando, FL (US); Gary Haberland, Winter Park, FL (US)

( * ) Notice: Subject to any disclaimer, the term of this patent is extended or adjusted under 35 U.S.C. 154(b) by 302 days.

(21) Appl. No.: 18/329,143

(22) Filed: Jun. 5, 2023

(65) Prior Publication Data

US 2024/0398442 A1 Dec. 5, 2024

(51) Int. Cl.

*A61B 17/42* (2006.01)
*A61B 17/34* (2006.01)
*A61B 17/00* (2006.01)

(52) U.S. Cl.

CPC ...... *A61B 17/4241* (2013.01); *A61B 17/3423* (2013.01); *A61B 2017/00287* (2013.01)

(58) Field of Classification Search

CPC ............ A61B 17/4241; A61B 17/3423; A61B 2017/00287; A61B 17/00234
See application file for complete search history.

(56) References Cited

U.S. PATENT DOCUMENTS

| | | | | |
|---|---|---|---|---|
| 5,486,183 | A * | 1/1996 | Middleman ...... | A61B 17/32056 606/127 |
| 5,935,098 | A * | 8/1999 | Blaisdell ............... | A61M 25/04 604/515 |
| 2019/0374212 | A1* | 12/2019 | Prior ................ | A61B 17/00234 |

* cited by examiner

*Primary Examiner* — Richard G Louis
(74) *Attorney, Agent, or Firm* — Dunlap Bennett & Ludwig, PLLC

(57) ABSTRACT

A laparoscopic assisted vaginal hysterectomy specimen retrieval device provides a plug assembly that rides along an outer circumference of the introducer tube. The plug assembly is moveable between a locked condition and an unlocked condition. A distal end of the plug assembly provides a seal portion dimensioned and adapted to engage a vaginal cavity in a sealed engagement, whereat a user may form a locked condition to prevent insufflated gas from escaping the vaginal cavity while the retrieval bag of the laparoscopic assisted vaginal hysterectomy specimen retrieval device is deployed, utilized, and retracted into the introducer tube.

5 Claims, 5 Drawing Sheets

LAPAROSCOPIC HYSTERECTOMY SPECIMEN RETRIEVAL DEVICE

BACKGROUND OF THE INVENTION

The present invention relates to laparoscopic retrieval processes and devices and more particularly, to a laparoscopic specimen retrieval system adapted for use in laparoscopic assisted vagina hysterectomies.

Hysterectomy is the partial or total surgical removal of the uterus. It may also involve removal of the cervix, ovaries, Fallopian tubes, and other surrounding structures.

During a vaginal hysterectomy, the surgeon may perform a colpotomy, creating an incision around the cervix, which may involve the removal of the cervix and uterine fundus, thereby creating an open area to aid in the laparoscopic process. Separately, during a hysterectomy, gases may be insufflated into the abdominal cavity to create a workspace, distending the cavity for more workroom for the surgeon.

In recent modern history, the preferred method of hysterectomy within most industrialized nations was accomplished through an abdominal procedure known as Laparoscopy in conjunction with a powered morcellator. Though another Laparoscopic method existed at that time, Laparoscopic Assisted Vaginal Hysterectomy (LAVH), it was not as popular as the method using a powered morcellator. This was in part because, through the powered morcellation method, the patient would have the option to maintain part of the cervix, which was not possible when completing the procedure via the LAVH method as the cervix would be completely removed.

Unfortunately, a known complication with the morcellation method, was that approximately 1/10,000 patients may have a hidden carcinoma, which would be eviscerated through the morcellation process and the cells from the carcinoma could then remain in the patient's pelvic region and possibly lead to terminal cancer as the anatomy was not contained to prevent the splatter of the morcellated cells. In time, the United States Food and Drug Agency (FDA) required the removal of powered morcellators from the clinical market, and most of the remaining industrialized global health care market followed this movement. As a result, the historically relatively minor utilization of the LAVH method, now grew in prominence.

A common problem in LAVH, however, is a loss of pneumoperitoneum (positive pressure within abdominal cavity) which occurs after the colpotomy procedure. The effect of the loss of pneumoperitoneum is that the surgeon, who is managing visualization within the abdominal cavity via a laparoscope, loses visual acuity. In other words, when the effect of the positive pressure, within the abdominal cavity, is compromised the surgeon loses the ability to maintain visualization of critical anatomical structures. This increases the risk of the procedure up to and including pulling the retrieved anatomy through the vaginal canal during the LAVH method.

Currently, medical practitioners stuff gauze or surgical sponges around the distal end of the laparoscopic retrieval bag device to prevent insufflated gas from escaping by way of the vaginal canal when retrieving hysterectomized organs and tissue. The makeshift process of plugging gaps aimed to prevent the escape of gas used to inflate the abdominal cavity during and following a colpotomy incision, with gauze or surgical sponges, can be time consuming, inefficient, and haphazard, which runs counter to the delicacy of laparoscopic surgery demanded in this anatomical area.

A need therefore exists for a specimen retrieval system embodying an intrinsic plug adapted for use in laparoscopic assisted vagina hysterectomies to reduce procedure time and waste as well as enable more surgical precision.

SUMMARY OF THE INVENTION

Using the present invention, following the colpotomy, the adjustable "plug" intrinsically associated with the specimen retrieval device, is inserted into the vaginal canal along with a substantial or entire portion of the specimen retrieval device. The intrinsic plug reestablishes the ability to manage positive pressure within the abdominal cavity and the necessary visualization. Then, after the anatomy is loaded into the collection bag by the surgeon, which is another intrinsic part of the specimen retrieval device of the present invention, the main introducer apparatus of the present invention is removed, along with the intrinsic plug, while simultaneously the surgeon would begin advancing the bagged anatomy into the now open area that the colpotomy created. At this point, the surgeon could either use the bagged anatomy as a "plug" itself and elect to continue with additional elements of the laparoscopic portion of the procedure, as pneumoperitoneum is maintained, decide to extract the anatomy from the retrieval bag using a cold knife method, or the anatomy could also then itself be small enough to be retrieved from the patient, passing through the vaginal canal within the retrieval bag. The surgeon would make this decision, but the present invention provides the surgeon these options.

The present invention includes a method of improving laparoscopic assisted vaginal hysterectomies (LAVH) through a device that embodies a standard laparoscopic retrieval bag mechanism with a plug assembly for sealing the vaginal canal during the LAVH.

The plug assembly includes a slidable and lockable plug dimensioned and adapted to create a seal, by way of a seal portion, to maintain insufflation after the colpotomy.

The mechanical design of the slide lock is not particularly limited. The slide lock may be any device or mechanism sufficient to toggle between a locked condition and an unlocked condition, including but not limited to a pinch clamp, screw clamp or the like. The locked condition prevents the plug from moving out of a sealed engagement with the vaginal canal/cavity.

The seal portion may be made of any soft, flexible, and durable material capable of forming a sealed engagement of a colpotomy hole. The seal portion can have many shapes, including round/oval shape, with a bevel or tapered profile to seal the colpotomy hole properly.

The shape of the handle is dimensioned and adapted to be ergonomically efficient for the user based on the patient position during the procedure.

In one aspect of the present invention, a laparoscopic assisted vaginal hysterectomy specimen retrieval device includes the following: an introducer tube; a plug assembly that slides along an outer circumference of the introducer tube, the plug assembly being moveable between a locked condition and an unlocked condition enabling sliding along said outer circumference; and a seal portion disposed along a distal end of the plug assembly dimensioned and adapted to occlude a vaginal canal of a laparoscopic patient in a sealed engagement, whereby the sealed engagement prevents insufflated gas from escaping the vaginal canal while the laparoscopic specimen retrieval device is utilized.

In another aspect of the present invention, the laparoscopic assisted vaginal hysterectomy specimen retrieval device further includes wherein the plug assembly further include a clamping apparatus for forming the locked condition, wherein the plug assembly further comprises an actuator member for moving between the locked and unlocked conditions, wherein the actuator member is disposed along a proximal end of the plug assembly, wherein the seal portion has a tapered profile facilitating the sealed engagement, wherein the tapered profile is defined, in part, by two or more rounded flanges of successively increasing diameters; and further including a retrieval bag movable between a retracted position and a deployed position relative to the introducer tube.

In yet another aspect of the present invention, a operatively associating a plug assembly along an outer circumference of an introducer tube of a vaginal hysterectomy specimen retrieval device so that plug assembly moves between a locked condition and an unlocked condition enabling the plug assembly to slide along said outer circumference to adjacent a distal end of the introducer tube, wherein the plug assembly has a seal portion dimensioned to seal the vaginal cavity of a laparoscopic assisted vaginal hysterectomy patient so as to occlude insufflated gas from escaping said vaginal cavity; inserting a distal end of the introducer tube having a retrieval bag into the vaginal cavity; and sliding the plug assembly to seal said vaginal cavity sufficient to prevent loss of pneumoperitoneum.

These and other features, aspects and advantages of the present invention will become better understood with reference to the following drawings, description, and claims.

DETAILED DESCRIPTION OF THE INVENTION

The following detailed description is of the best currently contemplated modes of carrying out exemplary embodiments of the invention. The description is not to be taken in a limiting sense but is made merely for the purpose of illustrating the general principles of the invention, since the scope of the invention is best defined by the appended claims.

Broadly, an embodiment of the present invention provides a laparoscopic assisted vaginal hysterectomy specimen retrieval device. The laparoscopic assisted vaginal hysterectomy specimen retrieval device provides a plug assembly that rides along an outer circumference of the introducer tube. The plug assembly is moveable between a locked condition and an unlocked condition. A distal end of the plug assembly provides a seal portion dimensioned and adapted to engage the vaginal cavity or canal in a sealed engagement, whereat a user may form a locked condition to prevent insufflated gas from escaping the vaginal cavity or canal while the retrieval bag of the laparoscopic assisted vaginal hysterectomy specimen retrieval device is deployed, utilized, and retracted into the introducer tube.

Figure 1:
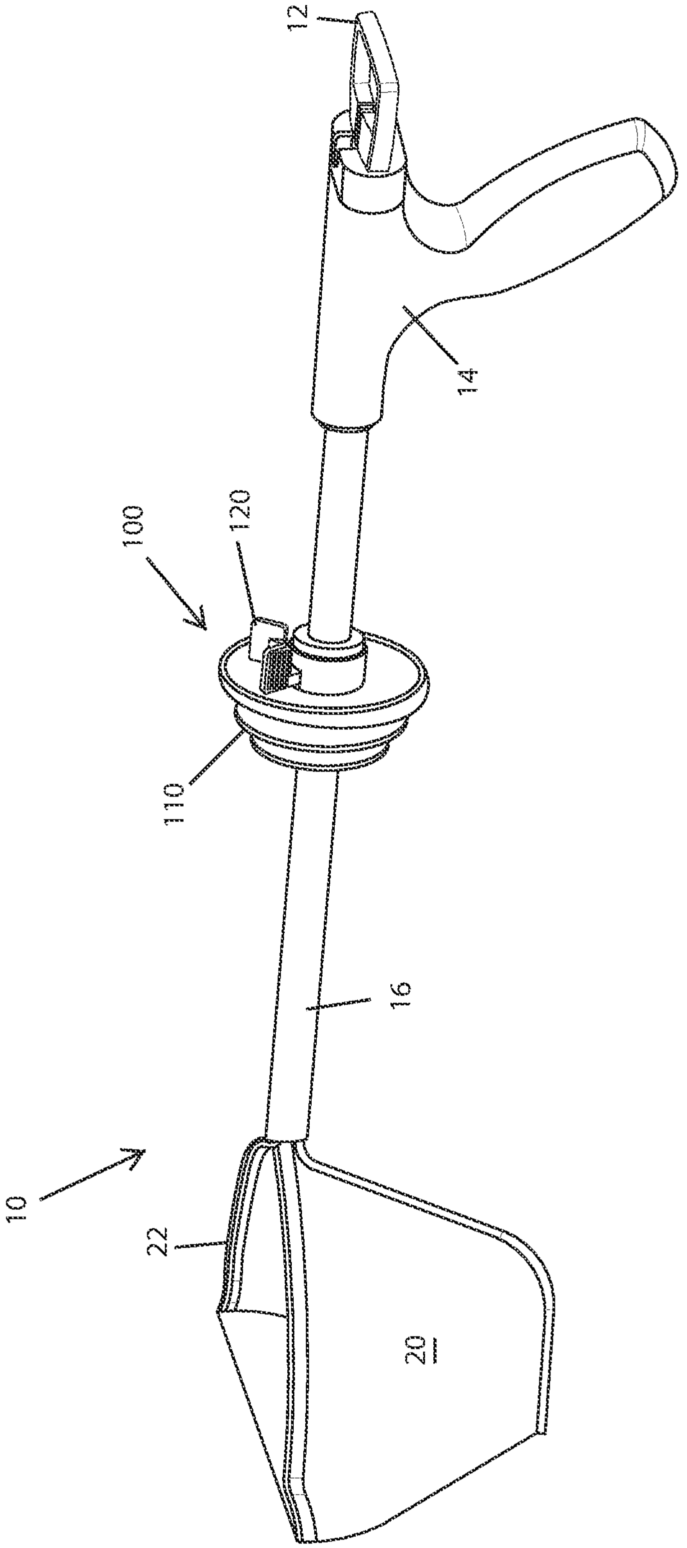
FIG. 1 is a rear perspective view of an exemplary embodiment of the present invention.
Figure 2:
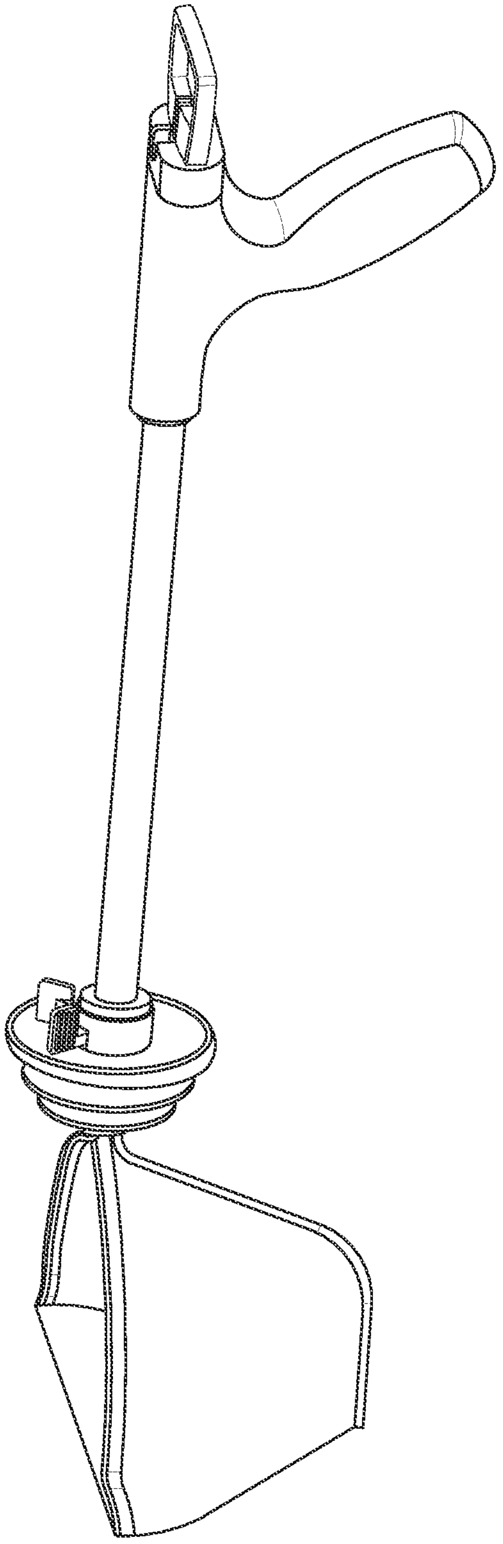
FIG. 2 is a rear perspective view of an exemplary embodiment of the present invention.
Figure 3:
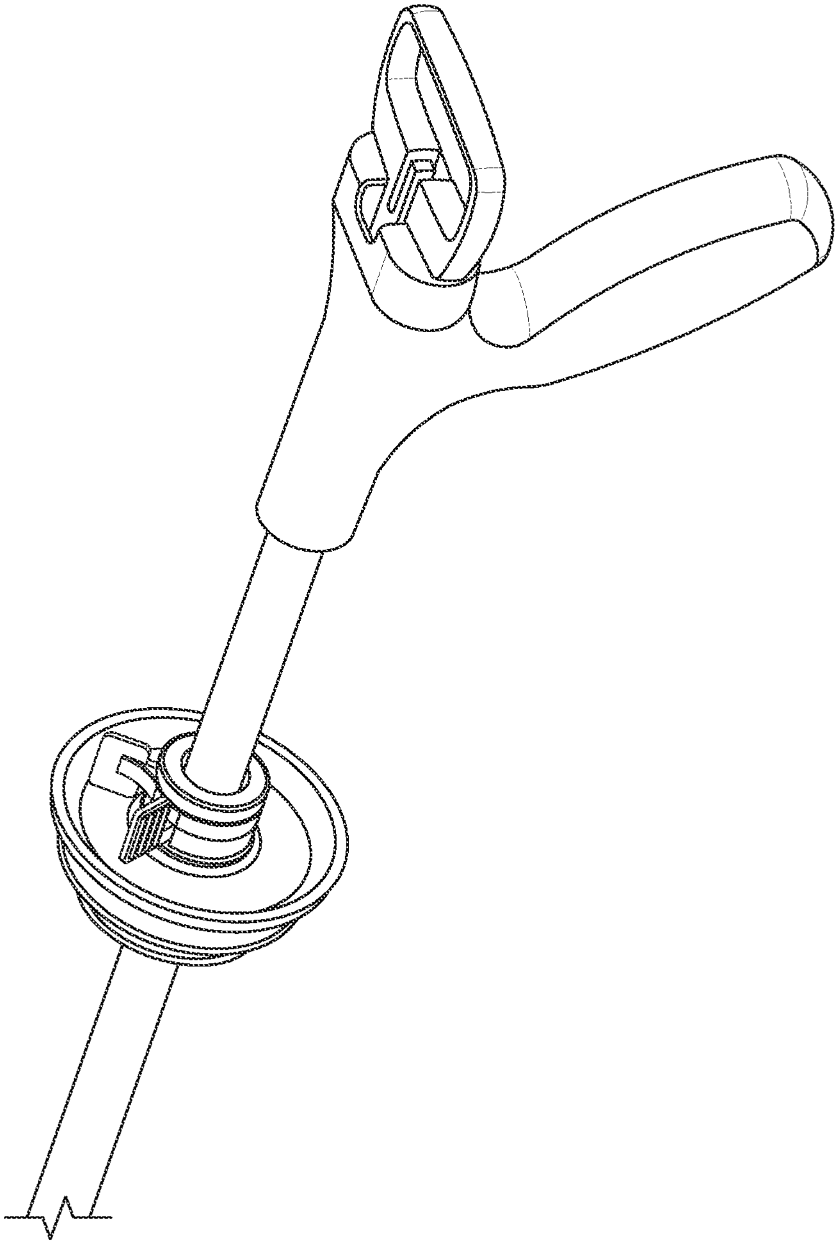
FIG. 3 is a detailed rear perspective view of an exemplary embodiment of the present invention.
Figure 4:
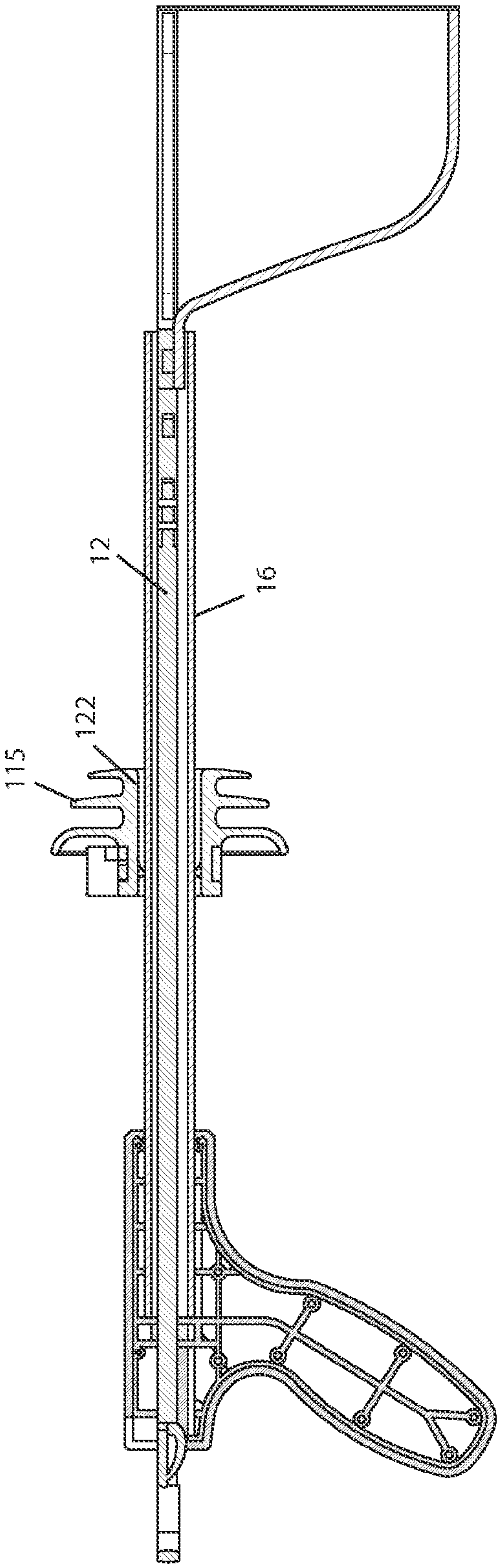
FIG. 4 is a cross-sectional view of an exemplary embodiment of the present invention, illustrating the plug assembly in an unlocked condition.
Figure 5:
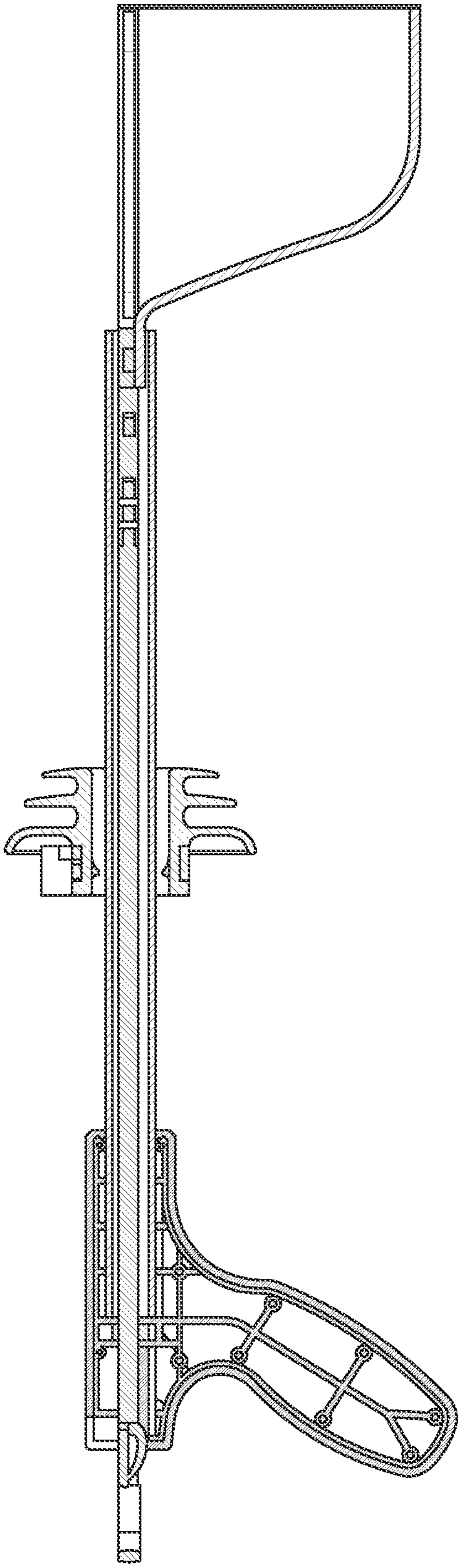
FIG. 5 is a cross-sectional view of an exemplary embodiment of the present invention, illustrating the plug assembly in a locked condition.

Referring to FIGS. 1-5, the present invention may include a v laparoscopic assisted vaginal hysterectomy specimen retrieval device 10. The device 10 comprises an actuator 12 (e.g., a push rod or the like), a handle 14, an introducer tube 16 and biasing arms 22 holding the retrieval bag 20. The retrieval bag 20 is attached to the biasing arms 22 of a retracting element that opens the retrieval bag 20 and the actuator 12 that enables the retrieval bag 20 to be retracted into the introducer tube 16.

A plug assembly 100 may be operatively associated with an outer surface of the introducer tube 16 to be moveable between a locked condition and an unlocked condition wherein the plug assembly 100 can slide or ride along the outer surface from a proximal end of the introducer tube 16 (approximately adjacent the handle 14) to a distal end of the introducer tube 16 adjacent the deployed retrieval bag 20. The locked condition can be formed through actuating a clamp apparatus 122 that secures to the outer surface of the introducer tube 16. The clamp apparatus 122 can be any known method or device of selectively locking to an outer circumferential surface of a tube. Typically the actuating element 120 for moving between the locked and unlocked conditions is disposed an a proximal end of the plug assembly 100.

Along the distal end of the plug assembly 100 is disposed the seal portion 110. The seal portion includes a soft silicone (or equivalent) seal that is dimensioned and adapted to have a tapered profile for wedging into and plugging in a sealed engagement the vaginal cavity or canal by urging the plug assembly 100 therein or there against. The shape and geometry of the seal portion 100 may be any shape or geometry that forms a sealed engagement of the vaginal cavity of a patient. The tapered profile may include a series of rounded or curled flanges 115 that successively increase in diameter as they are proximately set back.

As used in this application, the term "about" or "approximately" refers to a range of values within plus or minus 10% of the specified number. And the term "substantially" refers to up to 80% or more of an entirety. Recitation of ranges of values herein are not intended to be limiting, referring instead individually to any and all values falling within the range, unless otherwise indicated, and each separate value within such a range is incorporated into the specification as if it were individually recited herein.

For purposes of this disclosure, the term "aligned" means parallel, substantially parallel, or forming an angle of less than 35.0 degrees. For purposes of this disclosure, the term "transverse" means perpendicular, substantially perpendicular, or forming an angle between 55.0 and 125.0 degrees. Also, for purposes of this disclosure, the term "length" means the longest dimension of an object. Also, for purposes of this disclosure, the term "width" means the dimension of an object from side to side. For the purposes of this disclosure, the term "above" generally means superjacent, substantially superjacent, or higher than another object although not directly overlying the object. Further, for purposes of this disclosure, the term "mechanical communication" generally refers to components being in direct physical contact with each other or being in indirect physical contact with each other where movement of one component affect the position of the other.

The use of any and all examples, or exemplary language ("e.g.," "such as," or the like) provided herein, is intended merely to better illuminate the embodiments and does not pose a limitation on the scope of the embodiments or the claims. No language in the specification should be construed as indicating any unclaimed element as essential to the practice of the disclosed embodiments.

In the following description, it is understood that terms such as “first,” “second,” “top,” “bottom,” “up,” “down,” and the like, are words of convenience and are not to be construed as limiting terms unless specifically stated to the contrary.

It should be understood, of course, that the foregoing relates to exemplary embodiments of the invention and that modifications may be made without departing from the spirit and scope of the present invention.

What is claimed is:

1. A laparoscopic assisted vaginal hysterectomy specimen retrieval device, comprising:

an introducer tube having a retrieval bag adjacent its distal end;

a plug assembly that slides along an outer circumference of the introducer tube, the plug assembly being moveable between a locked condition and an unlocked condition enabling sliding along said outer circumference; and a seal portion disposed along a distal end of the plug assembly dimensioned and adapted to occlude a vaginal cavity of a laparoscopic patient in a sealed engagement, whereby the sealed engagement prevents insufflated gas from escaping the vaginal cavity while the laparoscopic assisted vaginal hysterectomy specimen retrieval device is utilized, wherein the plug assembly further comprises a clamping apparatus for forming the locked condition, and wherein the plug assembly further comprises an actuator member for moving between the locked and unlocked conditions.

2. The laparoscopic assisted vaginal hysterectomy specimen retrieval device of claim 1, wherein the actuator member is disposed along a proximal end of the plug assembly.

3. The laparoscopic assisted vaginal hysterectomy specimen retrieval device of claim 2, wherein the seal portion has a tapered profile facilitating the sealed engagement.

4. The laparoscopic assisted vaginal hysterectomy specimen retrieval device of claim 3, wherein the tapered profile is defined, in part, by two or more rounded flanges of different diameters.

5. The laparoscopic assisted vaginal hysterectomy specimen retrieval device of claim 4, further comprising a retrieval bag movable between a retracted position and a deployed position relative to the introducer tube.

* * * * *